US011660581B2

(12) United States Patent
Mancosky et al.

(10) Patent No.: US 11,660,581 B2
(45) Date of Patent: May 30, 2023

(54) SYSTEM AND METHOD FOR TREATMENT OF PLANTS FOR SYNTHESIS OF COMPOUNDS THEREFROM

(71) Applicant: Hydro Dynamics, Inc., Rome, GA (US)

(72) Inventors: Douglas Mancosky, White, GA (US); John MacKay, Whitinsville, MA (US)

(73) Assignee: Hydro Dynamics, Inc., Rome, GA (US)

( * ) Notice: Subject to any disclaimer, the term of this patent is extended or adjusted under 35 U.S.C. 154(b) by 123 days.

(21) Appl. No.: 17/242,503

(22) Filed: Apr. 28, 2021

(65) Prior Publication Data

US 2021/0339218 A1 Nov. 4, 2021

Related U.S. Application Data

(60) Provisional application No. 63/017,774, filed on Apr. 30, 2020.

(51) Int. Cl.
| | | |
|---|---|---|
| *B01J 19/00* | (2006.01) | |
| *B01J 19/12* | (2006.01) | |
| *C07C 65/03* | (2006.01) | |
| *B01J 19/24* | (2006.01) | |
| *C07D 311/80* | (2006.01) | |
| *C07D 311/94* | (2006.01) | |

(52) U.S. Cl.
CPC ......... *B01J 19/008* (2013.01); *B01J 19/0066* (2013.01); *B01J 19/123* (2013.01); *B01J 19/2415* (2013.01); *C07C 65/03* (2013.01); *C07D 311/80* (2013.01); *C07D 311/94* (2013.01); *B01J 2219/00051* (2013.01); *B01J 2219/00162* (2013.01)

(58) Field of Classification Search
CPC ...... B01J 19/008; B01J 19/006; B01J 19/123; C07C 65/03
See application file for complete search history.

(56) References Cited

U.S. PATENT DOCUMENTS

| | | |
|---|---|---|
| 1,758,207 A | 5/1930 | Walker |
| 2,283,244 A | 5/1942 | Walker |
| 4,213,332 A | 7/1980 | Bonomo |
| 4,529,794 A | 7/1985 | Sortwell et al. |
| 4,864,872 A | 9/1989 | Stahl |
| 5,183,513 A | 2/1993 | Sajewski |
| 5,184,576 A | 2/1993 | Sajewski |
| 5,188,090 A | 2/1993 | Griggs |
| 5,239,948 A | 8/1993 | Sajewski |
| 5,265,629 A | 11/1993 | Sajewski |
| 5,380,411 A | 1/1995 | Schlief et al. |
| 5,385,298 A | 1/1995 | Griggs |
| 5,571,975 A | 11/1996 | Smith et al. |
| 5,605,587 A | 2/1997 | Meckling |
| 5,957,122 A | 9/1999 | Griggs |
| 6,221,206 B1 | 4/2001 | Bokstrom et al. |
| 6,365,555 B1 | 4/2002 | Moser et al. |
| 6,627,784 B2 | 9/2003 | Hudson et al. |
| 7,360,755 B2 | 4/2008 | Hudson et al. |
| 7,507,014 B1 | 3/2009 | League et al. |
| 7,771,582 B2 | 8/2010 | Kazem |
| 8,430,968 B2 | 4/2013 | Mancosky et al. |
| 8,465,642 B2 | 6/2013 | Kezem |
| 9,469,548 B2 | 10/2016 | Mancosky |
| 10,011,804 B2 | 7/2018 | Mancosky |
| 10,173,191 B2 | 1/2019 | Parker et al. |
| 10,220,365 B2 | 3/2019 | Mancosky |
| 10,557,105 B1 * | 2/2020 | Tran ........................ C11B 1/104 |
| 2005/0042129 A1 | 2/2005 | Kazem |
| 2005/0067122 A1 | 3/2005 | Kazem et al. |
| 2005/0087315 A1 | 4/2005 | Donovan et al. |
| 2007/0144785 A1 | 6/2007 | Smith et al. |
| 2007/0215346 A1 | 9/2007 | Sloan |
| 2008/0167204 A1 | 7/2008 | Slabaugh et al. |
| 2009/0166171 A1 | 7/2009 | Smith et al. |
| 2009/0235664 A1 | 9/2009 | Smith |
| 2010/0090124 A1 | 4/2010 | Kazem |
| 2013/0188295 A1 | 7/2013 | Chacko |
| 2014/0220179 A1 | 8/2014 | Matsui et al. |
| 2016/0059194 A1 | 3/2016 | Smith |
| 2016/0312099 A1 | 10/2016 | Armstead |
| 2016/0333652 A1 | 11/2016 | Mancosky |
| 2016/0339400 A1 | 11/2016 | Smith |
| 2017/0136427 A1 | 5/2017 | Smith |
| 2018/0320118 A1 | 11/2018 | Mancosky |
| 2019/0169479 A1 | 6/2019 | Armstead et al. |
| 2020/0121748 A1 | 4/2020 | Guerrazzi et al. |
| 2020/0122102 A1 | 4/2020 | Tumey |

FOREIGN PATENT DOCUMENTS

| | | |
|---|---|---|
| CN | 110452095 A | 11/2019 |
| JP | 55-102491 | 8/1980 |
| JP | 60-226594 | 11/1985 |
| JP | 62-213895 | 9/1987 |
| WO | WO2011/084392 A1 | 7/2011 |
| WO | WO2018/061009 A1 | 4/2018 |

OTHER PUBLICATIONS

SPX Corporation; *The APV Cavitator*; Brochure—Issued Oct. 2011—5003-01-10-2011-US; Copyright 2011, 2013 SPX Corporation.
SPX Corporation; *APV Cavitator Technology in Hydration of Hydrocolloids and Proteins*; Brochure—Issued Apr. 2013—16021-01-4-2013-US; Copyright 2013 SPX Corporation.

(Continued)

*Primary Examiner* — Sikarl A Witherspoon
(74) *Attorney, Agent, or Firm* — Womble Bond Dickinson (US) LLP

(57) ABSTRACT

Systems and methods for the treatment of plants, including decarboxylation, photo-oxidation, oxidation and/or combinations thereof, of cannabis and hemp plants and oils for biosynthesizing THCA, CBDA, and CBCA from CBGA are disclosed. A cannabinoid compound solution is fed into a cavitation zone of a controlled cavitation apparatus where the cannabinoid compound solution is subjected to cavitation and interaction with UV light for conversion of the cannabinoid compound solution to form a synthesized cannabinoid THC, CBD, CBC, CBG, CBNA, CBEA, CBLA product, or combinations thereof.

29 Claims, 3 Drawing Sheets

(56) References Cited

OTHER PUBLICATIONS

SPX Corporation; *APV Cavitator Technology in Functionalization of WPC and other Food Ingredients*; Brochure—Issued May 2013—16024-01-05-2013-US; Copyright 2013 SPX Corporation.
SPX Corporation; *APV Cavitator Technology for Ice Cream Mix Production*; Brochure—Issued Feb. 2013—16019-01-02-2013; Copyright 2013 SPX Corporation.
SPX Corporation; *APV Cavitator Technology for Toothpaste Production*; Brochure—Issued Feb. 2013—16018-01-02-2013; Copyright 2013 SPX Corporation.
SPX Corporation; *APV Cavitator Technology in Personal Care Processing*; Brochure—APV—16028 Version Jan. 2013 Issued Jul. 2013; Copyright 2013 SPX Corporation.
International Search Report and Written Opinion for International Patent Application No. PCT/US2016/028873 dated Jul. 19, 2016.
International Preliminary Report on Patentability in International Patent Application No. PCT/US2016/028873 dated Nov. 2, 2017.
Wang, M. et al.; Decarboxylation Study of Acidic Cannabinoids; A Novel Approach Using Ultra-High-Performance Supercritical Fluid Chromatography/Photodiode Array-Mass Spectrometry; Cannabis and Cannabinoid Research; 2016; vol. 1.1, pp. 262-271.
International Search Report and Written Opinion, PCT Application No. PCT/US2021/029597 dated Aug. 11, 2021.

\* cited by examiner

SYSTEM AND METHOD FOR TREATMENT OF PLANTS FOR SYNTHESIS OF COMPOUNDS THEREFROM

REFERENCE TO RELATED APPLICATIONS

The present Patent application claims the benefit of U.S. Provisional Patent Application No. 63/017,774, filed on Apr. 30, 2020.

INCORPORATION BY REFERENCE

The disclosures made in U.S. Provisional Patent Application No. 63/017,774, filed on Apr. 30, 2020 are specifically incorporated by reference herein as if set forth in their entireties.

TECHNICAL FIELD

This provisional patent disclosure relates generally to systems and methods for the treatment of plants; and in particular to a system, apparatus and method for treatment of cannabis and hemp plants and oils for biosynthesizing THCA, CBDA, and CBCA from CBGA.

BACKGROUND

Cannabis and hemp plants biosynthesize Tettrahydrocannabolic acid (THCA), Cannabidiolic acid (CBDA), and Cannabichromeric acid (CBDA) from Cannabigerolic acid (CBGA). Although these biosynthesized forms have demonstrated potential value for medical conditions, the majority of the research has been done using the decarboxylated form of the compounds (THC, CBD, CBC and CBG) which are more biologically active in the body. The conversion of these cannabinoid compounds from the "acid form" involves the loss of carbon dioxide.

For example, there are two primary routes to decarboxylation of cannabis and/or hemp. The first is heat, which mimics incineration found in smoking or baking. One of the critical challenges with heat is obtaining precision control of the heating of the plant or oil so as to minimize the degradation of the newly decarboxylated forms due to excessive heat. A second challenge is the loss of any other volatile compounds during the process, such as the terpene compounds. Common methods of heating include the use of ovens, oil baths or hot water baths of 200-300 degrees F. for about 15 minutes to about 4 hours. At low temperatures, the degradation has been found to be less, but the yield is lower, while at higher temperatures, greater or more significant degradation is common.

A second option for decarboxylation is the use of light. The effect of light is commonly seen in the differences between indoor and outdoor plants, where the outdoor plants typically have a small percentage of the decarboxylated form due to the exposure to direct sunlight, as indicated, for example, by the following reaction:

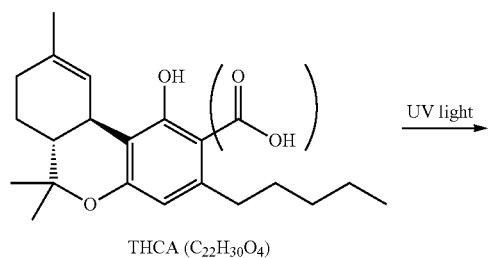

THCA ($C_{22}H_{30}O_4$)

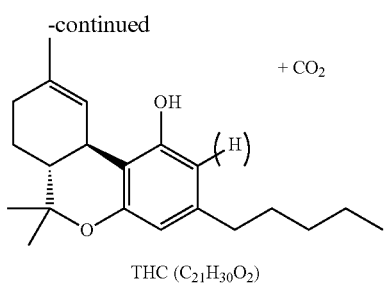

THC ($C_{21}H_{30}O_2$)

When using direct Ultraviolet (UV) light on plants and oils, however, the energy from the UV light generally will only pass a few millimeters into the sample. This would potentially only allow a small portion of the sample to decarboxylase. The UV light's energy to decarboxylase plants and oils further can be compromised due to the viscosity and color of an oil.

Accordingly, it can be seen that a need exists for a system and method of treatment of plants such as cannabis and hemp plants, such as by decarboxylation, photo-oxidation, oxidation and/or combinations thereof, for biosynthesis, and other related and unrelated problems in the art.

SUMMARY

Briefly described, the present disclosure relates to systems and methods for the treatment of plants; and in particular to a system, apparatus and method for treatment, including decarboxylation, photo-oxidation, oxidation and/or combinations thereof, of cannabis and hemp plants and oils for biosynthesizing THCA, CBDA, and CBCA from CBGA. In one embodiment, a controlled cavitation apparatus is utilized for decarboxylating a cannabinoid compound solution using controlled hydrodynamic cavitation.

For example, in embodiments, the cavitation apparatus will include a cylindrical housing having an interior wall, a cylindrical rotor having a peripheral surface rotatably mounted in the housing, an inlet, an outlet, and an internal cavitation zone. The cavitation zone generally will be formed between the peripheral surface of the rotor and the interior wall of the housing. The cannabinoid compound solution will be introduced into and caused to flow through the cavitation apparatus in such a way that the solution moves through the cavitation zone. Cavitation is generated within the cannabinoid compound solution in the cavitation zone by controlling operation of the cavitation apparatus. In embodiments, and for some cannabinoids, the cavitation can be controlled so as to induce nucleation of the compound to form seed crystals. In embodiments, the cavitation apparatus has a transparent housing allowing for the transmission of UV light into the cavitation zone, and cavitation of the cannabinoid compound solution is controlled by varying the RPM of the rotor between about 0 RPM and about 3600 RPM to optimize UV reaction while minimizing temperature and shear degradation. The rate of rotation of the rotor is further controlled for controlling the cavitation and refreshing of the cannabinoid compound solution along the area of the housing exposed to UV light; and for promoting decarboxylation of the cannabinoid compound solution to form a decarboxylated cannabinoid THC, CBD, CBC or CBG product through interaction with UV light. In addition, for cannabinoid compound solutions where seed crystals are formed, cavitation further can be controlled for distributing the seed crystals substantially uniformly throughout the cannabinoid compound solution;

In some embodiments, generating cavitation within the cannabinoid compound solution is conducted at low temperature. In other embodiments, generating cavitation within the cannabinoid compound solution is conducted at low pressure.

Additionally, in embodiments, causing the cannabinoid compound solution to flow through the cavitation apparatus comprises feeding the cannabinoid compound solution in a substantially continuous fluid stream through the cavitation zone.

Still further, in embodiments, the cannabinoid compound solution comprises an aqueous cannabinoid solution. In some embodiments, the cannabinoid compound solution comprises a viscous stream. In other embodiments, the cannabinoid compound solution comprises a stream containing solids. In addition, in embodiments, the cannabinoid compound solution comprises a solution that is opaque. Still further, in embodiments, the cannabinoid compound solution comprises a solution of THCA, CBDA, or CBCA biosynthesized from CBGA.

In another aspect, an apparatus and method are disclosed for converting compounds such as THCA, CBDA and CBCA to CBNA, CBEA and CBLA through chemical processes such as photo-oxidation, oxidation and UV light. In embodiments, the method includes the steps of processing at least one stream of a feed solution of a cannabinoid compound to be converted and passing the stream through the cavitation zone of a cavitation apparatus, with the stream of the cannabinoid compound solution further treated with and/or subjected to addition of oxidants, UV light or electrochemistry.

The cavitation apparatus generally will include a rotor within a housing or stator, with one or more walls of the cavitation apparatus including a substantially transparent wall or portion thereof. In embodiments, the surface of the rotor is provided with a multitude of shallow radial bores (or other cavitation producing features) and the movement of these bores induces intense cavitation events in the cannabinoid compound solution within the bores. The energy and pressure of the cavitation events within the flow of feed stock cannabinoid compound solution causes intense mixing and fast refreshing of the fluid layer of the cannabinoid compound on the outer wall surface where it is exposed to oxidants, electrodes, UV light, and/or combinations thereof, to promote conversion of the cannabinoid compound such as THCA, CBDA and CBCA to CBNA, CBEA and CBLA to form a synthesized cannabinoid THC, CBD, CBC, CBG, CBNA, CBEA, CBLA product, or combinations thereof. Repeat cycling of the flow through the cavitation zone of the cavitation device can cause further conversion of the process fluid.

In some aspects, a method of converting a cannabinoid compound solution using controlled hydrodynamic cavitation comprises the steps of feeding a stream of the cannabinoid compound solution into a cavitation apparatus having an inlet, an outlet, a rotor having a series of cavitation inducing features therealong, and a cavitation cavity or stator with one or more transparent outer walls and within which a cavitation cavity zone is defined; directing the cannabinoid compound solution to flow through the cavitation zone of the cavitation apparatus; generating cavitation within the cannabinoid compound solution in the cavitation zone; during cavitation, subjecting the cannabinoid compound solution to UV light transmitted through the one or more transparent outer walls; and promoting conversion of the cannabinoid compound solution to form a synthesized cannabinoid THC, CBD, CBC, CBG, CBNA, CBEA, CBLA product, or combinations thereof through interaction with UV light, with oxygen, with reagents, or combinations thereof. In some embodiments, the cavitation further can be controlled for distributing cannabinoid seed crystals formed in the cannabinoid compound solution substantially uniformly throughout the cannabinoid compound solution;

In embodiments of the method, generating cavitation within the cannabinoid compound solution is conducted at a temperature of approximately 100°-130° Celsius. In other embodiments, generating cavitation within the cannabinoid compound solution is conducted at a pressure of approximately 1 psi to approximately 50 psi.

In embodiments, cavitation generated within the cannabinoid compound solution is controlled by varying the RPM of the rotor between about 0 RPM and about 3600 RPM to optimize UV reaction while minimizing temperature and shear degradation. In addition, in embodiments, directing the cannabinoid compound solution to flow through the cavitation apparatus comprises feeding the cannabinoid compound solution in a substantially continuous fluid stream of the cannabinoid compound solution through the inlet and into the cavitation cavity or stator where the cannabinoid compound solution passes between the rotor and the cavitation cavity or stator.

In embodiments, the cannabinoid compound solution comprises an "crude" cannabinoid solution containing multiple cannabinoids, terpenes and other chemical compounds extracted from cannabis. In other embodiments, the stream of the cannabinoid compound solution comprises a viscous stream. In some embodiments, the stream of the cannabinoid compound solution comprises solid materials. In other embodiments, the cannabinoid compound solution comprises a solution that is opaque. Additionally, the cannabinoid compound solution can comprise a solution of THCA, CBDA, or CBCA biosynthesized from CBGA.

In embodiments, promoting conversion of the cannabinoid compound solution comprises decarboxylating the cannabinoid compound solution to form synthesized cannabinoid THC, CBD, CBC, CBG, or combinations thereof, through interaction of the cannabinoid compound with UV light. In some embodiments, promoting conversion of the cannabinoid compound solution comprises decarboxylating a CBCA compound to CBLA through interaction with UV light. In other embodiments, promoting conversion of the cannabinoid compound solution comprises promoting oxidation of a THCA compound to CBNA through interaction with oxygen or other oxidative species either added or created in situ. In embodiments, promoting conversion of the cannabinoid compound solution comprises promoting oxidation of a CBDA compound to CBEA through interaction with UV light.

In embodiments, the cavitation apparatus comprises electrodes configured to enable electrochemistry and the production oxidative species in situ within the cannabinoid compound solution. In additional embodiments, the oxidative species comprise ozone, peroxide, radicals, or combinations thereof. In other embodiments, feeding the stream of the cannabinoid compound solution comprises feeding a substantially consistent flow of the cannabinoid compound solution through the cavitation zone.

In other embodiments, promoting conversion of the cannabinoid compound solution comprises exposing the cannabinoid compound solution to UV light and to ozone or other reactant to promote pasteurization of the cannabinoid compound solution. Additionally, in embodiments, generating cavitation within the cannabinoid compound solution in the cavitation zone further comprises subjecting the cannabinoid compound solution to cavitation events sufficient to induce nucleation of the cannabinoid compound solution to form seed crystals therein.

Accordingly, a system and method for decarboxylation of plants, including decarboxylation of cannabis and hemp plants and oils for biosynthesizing THCA, CBDA, and CBCA from CBGA are disclosed that satisfy the above mentioned and other needs, and that provide other potential advantages heretofore not common in construction. The foregoing and various other features, aspects and advantages of the present disclosure will be further understood upon a review the following detailed description, when taken in conjunction with the accompanying drawing figures, which are briefly described as follows.

BRIEF DESCRIPTION OF THE DRAWINGS

It will be appreciated that for simplicity and clarity of illustration, elements illustrated in the figure are not necessarily drawn to scale. For example, the dimensions of some elements may be exaggerated relative to other elements. As those skilled in the art also will appreciate and understand, the dimensions of various features and elements of the drawings may be expanded and/or reduced to more clearly illustrate the embodiments of the present disclosure as described herein. Accordingly, embodiments incorporating the teachings of the present disclosure are shown and described below with respect to the drawings, in which.

DISCUSSION OF THE PRESENT DISCLOSURE

Cannabis and Hemp plants naturally biosynthesize THCA, CBDA, and CBCA from CBGA. An apparatus, system and associated method are disclosed for treatment of cannabinoid compounds such as THCA, CBDA and CBCA to CBNA, CBEA and CBLA to form a synthesized cannabinoid THC, CBD, CBC, CBG, CBNA, CBEA, CBLA product, or combinations thereof, such as by decarboxylation, photo-oxidation, oxidation and/or combinations thereof, of cannabinoid compounds such as THCA, CBDA and CBCA to CBNA, CBEA and CBLA in cannabis and hemp. More specifically, an apparatus and method are disclosed for decarboxylation, photo-oxidation, oxidation and/or other synthesis of THCA, CBDA and CBCA to CBNA, CBEA and CBLA, and/or other cannabinoid compounds from cannabis and/or hemp plants and oils using hydrodynamic cavitation and the application of UV light, interaction with oxygen or oxidative species, and/or combinations thereof. It will be understood that the following description taken in combination with the accompanying drawing figures is provided to assist in the understanding of the teachings disclosed herein. The description is directed to various implementations and embodiments of the present disclosure, and is provided to assist in describing such teachings, but such implementations and embodiments should not be interpreted as a limitation on the scope or applicability of the present disclosure.

Figure 1:
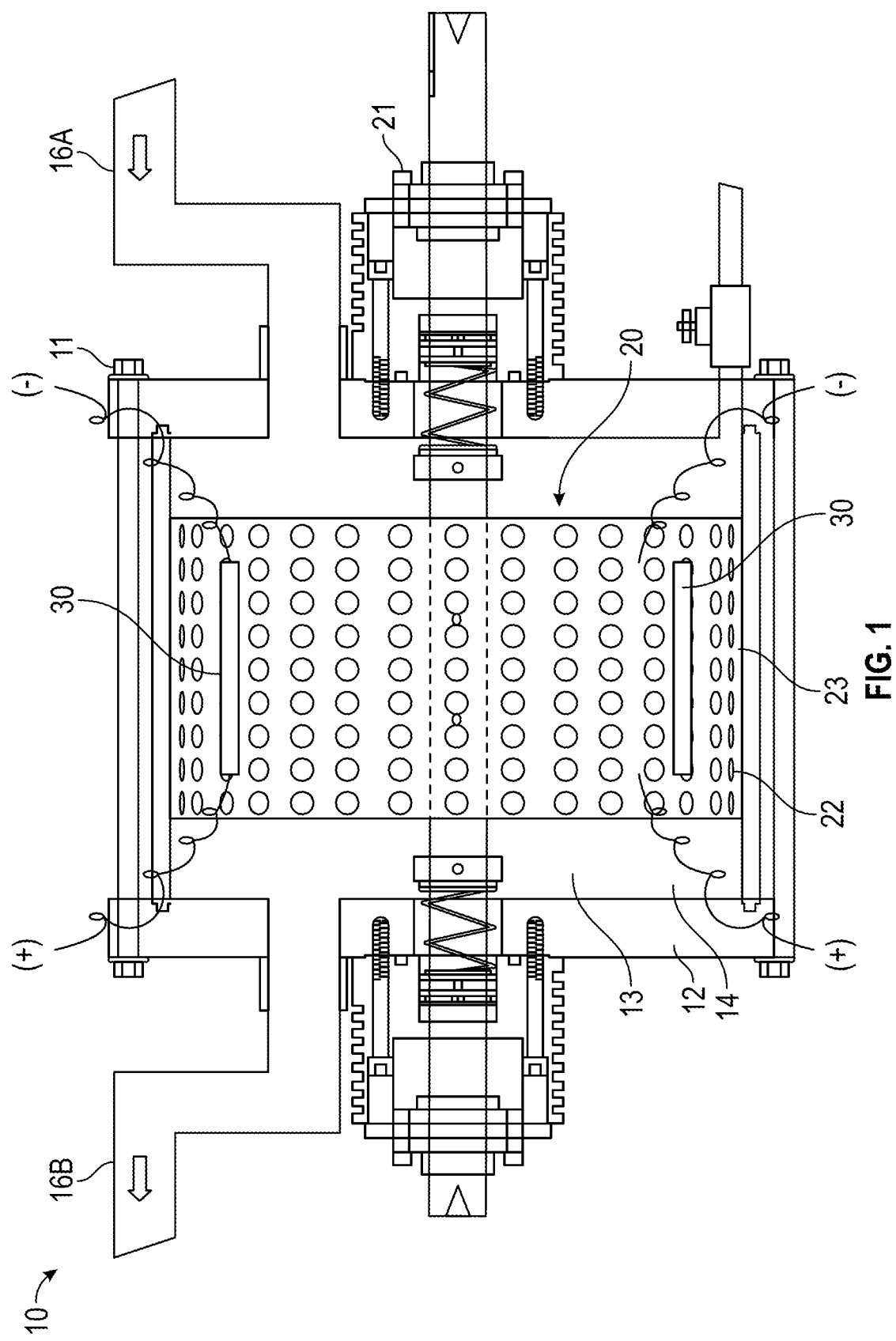
FIG. 1 is a schematic illustration of one embodiment of a hydrodynamic cavitation system or apparatus for the decarboxylation of cannabis and hemp plants and oils according to principles of the present disclosure.

FIG. 1 illustrates an embodiment of a hydrodynamic cavitation system or apparatus 10 for the decarboxylation, photo-oxidation, oxidation or other treatment of cannabis and hemp plants and oils according to the present disclosure. The hydrodynamic cavitation apparatus can, in one embodiment, comprise a hydrodynamic cavitation apparatus as disclosed in U.S. Pat. No. 10,011,804 and United States Patent Publication Nos. YW6454344=4568E5$erh$ 2019/0169479A1, the disclosures of which is incorporated by reference as if set forth fully herein.

As shown in FIG. 1, the hydrodynamic cavitation apparatus 10, in one aspect, will include a housing 11 having or defining a cavitation cavity or stator 12 with one or more transparent outer walls 13, and within which a cavitation cavity or zone 14 is defined, the cavitation cavity having an inlet 16A and an outlet 16B. A rotor 20 is provided and rotates within the cavitation zone of the cavitation cavity or stator. The rotor will be driven by a motor or other drive 21, and can be controller to operate at varying speeds as needed or selected for a particular cannabinoid compound being treated, and/or the treatment or process being applied thereto. As indicated in FIG. 1, at least an outer surface 22 of the rotor 20 is provided with a multitude of shallow radial bores 23 (or other cavitation producing features). The rotation of the rotor within the cavitation housing and with respect to the stator or cavitation cavity 12 induces cavitation of a cannabinoid compound solution/fluid within the bores of the rotor.

The transparent outer wall 13 of the cavitation cavity 12 can include at least a portion thereof formed from a transparent material. For example, and without limitation, at least one side wall can be formed from a substantially transparent material, or one or more of the side walls can include windows or sections formed from a substantially transparent material that is configured to allow UV light to pass therethrough. One or more UV light sources 30 will be provided adjacent the cavitation cavity and applies UV light through the transparent outer wall 13 of the housing so as to interact with a cannabinoid compound feed solution undergoing cavitation events within the cavitation apparatus. In one embodiment, UV light in a range of up to about 1,000 $J/m^2$ can be used.

Figure 2:
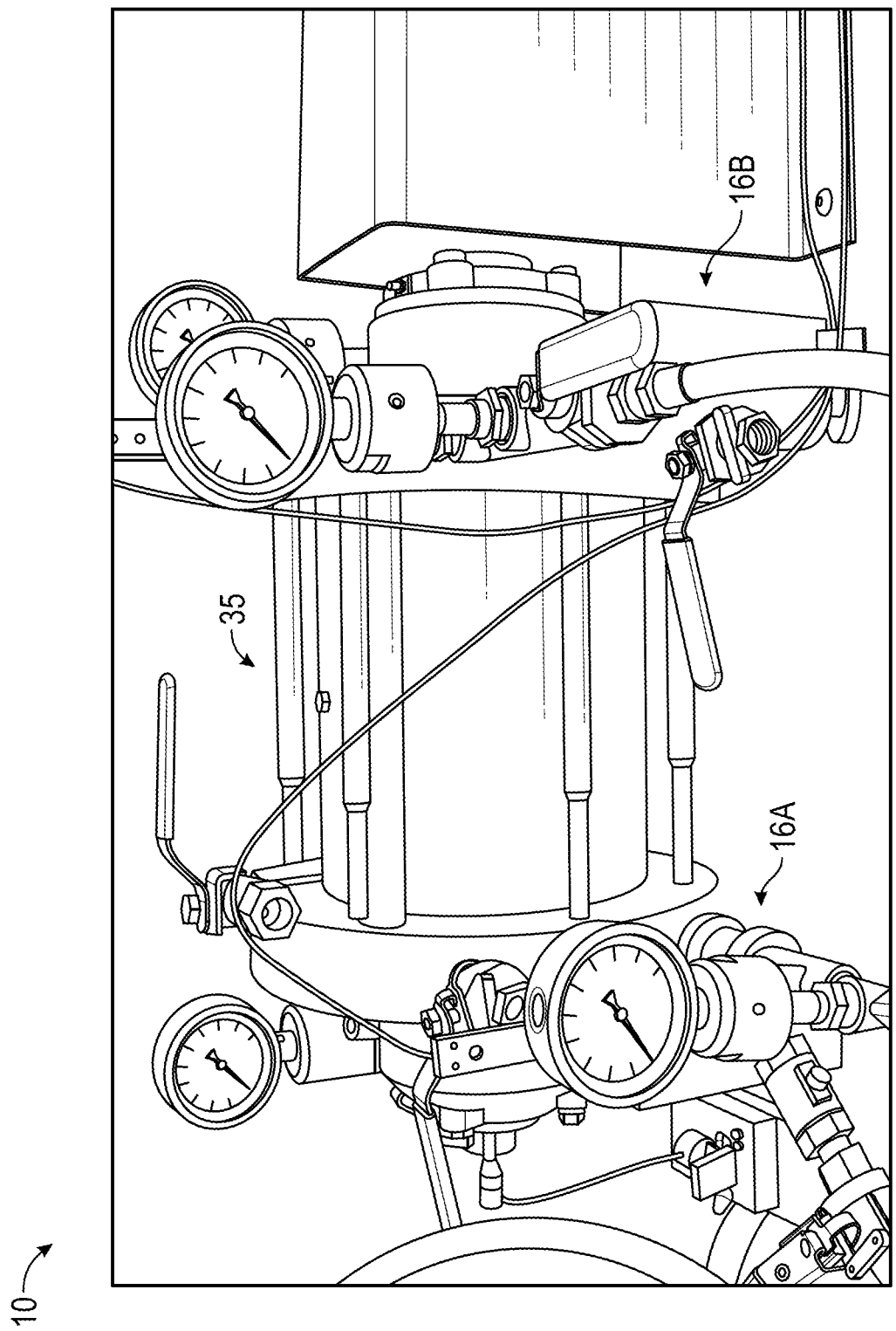
FIG. 2 illustrates an apparatus for generating electrochemistry in a flow of feed stock solution according to principles of the present disclosure.

In addition, electrodes 35 (FIG. 2) can also be provided within the cavitation cavity or zone 14. For example, one or more sets of electrodes can be provided at spaced locations along the cavitation cavity or zone. The electrodes will be configured for enabling electrochemistry and the production oxidative species in situ, with such oxidative species including materials such as ozone, peroxide or radicals. For example, FIG. 2 shows a cavitation apparatus for generating electrochemistry in a flow of a cannabinoid compound feed stock solution, with electrical connections provided therealong. The apparatus further can include insulating materials along an outer side wall thereof and pressure control valves and monitoring gauges/sensors for monitoring the flow/stream of the FIG. 2 shows an additional cavitation apparatus 10 for generating electrochemistry in a flow of the cannabinoid compound feed stock solution into and out of the apparatus.

The rotor-stator design of the cavitation apparatus 10 allows for high flow rates of the cannabinoid compound solution feed stock, and feed stock solutions that can be opaque, contain solids or have high viscosity. Further, the cavitation device operates substantially continuously, making it suitable for conversion of cannabinoid compounds within a feed stock cannabinoid compound solution at commercially desirable flow rates. The process further can be tuned to provide highly reliable results and high yield. The process is aided by the low temperature, low pressure and low shear environment of the cavitation zone as to not damage other compounds of interest. For example, movement of the bores or other cavitation producing features of the rotor of the cavitation device with respect to the stator or housing wall of the cavitation device induces intense cavitation events in the cannabinoid compound solution within the bores. The energy and pressure of the cavitation events within the flow of feed stock cannabinoid compound solution causes intense mixing and fast refreshing of the fluid layer of the cannabinoid compound solution on the outer wall surface exposed to the oxidants, electrodes or UV light allowing for conversion. Repeat cycling of the flow through the cavitation zone of the device can cause further conversion of the process fluid of the cannabinoid compound solution.

In one embodiment, the method includes the steps of processing at least one stream of a feed solution of THCA and/or other cannabinoid compounds from cannabis and/or hemp plants and oils to be decarboxylated using hydrodynamic cavitation, including passing the feed solution stream through the cavitation zone between the spinning rotor and outer transparent cavity wall of the hydrodynamic cavitation apparatus. In some embodiments, the cannabinoid compound solution comprises a solution of THCA, CBDA, or CBCA biosynthesized from CBGA; and in embodiments, can comprise a "crude" cannabinoid solution containing multiple cannabinoids, terpenes and other chemical compounds extracted from cannabis. Hydrodynamic cavitation is induced within the cavitation zone between the spinning rotor and the outer wall (or other wall) of the cylindrical cavitation cavity or stator within which the rotor spins with another outer wall of the cavitation cavity being transparent to UV light. A UV light source positioned outside the transparent outer wall and applies UV light energy to the feed solution stream.

As the UV light is applied, the movement of multitude of shallow radial bores (or other cavitation producing features) provided within the surface of the rotor induces intense cavitation events in the solution within the bores. The energy and pressure of the cavitation events generated within the flow of feed stock solution causes intense mixing and fast refreshing of the fluid layer on the cavitation cavity outer wall surface that is exposed to the UV light, allowing for decarboxylation. Moreover, faster rotor speeds lead to a faster refreshing of the fluid at the surface which is exposed to the UV light. As speed increases, the rate of decarboxylation would be expected to increase until the surface refresh or mass transfer are no longer a substantial limiting factor in the reaction rate. Therefore, controlling the cavitation can be used to control decarboxylation. Repeat cycling of the flow of the feed solution stream through the cavitation zone of the device can cause further decarboxylation of the processed feed solution.

Cavitation is generated within the cannabinoid compound solution in the cavitation zone by controlling operation of the cavitation apparatus. Cavitation of the cannabinoid compound solution is controlled by varying the RPM of the rotor between about 0 RPM and about 3600 RPM to optimize UV reaction with the cannabinoid compound solution while minimizing temperature and shear degradation. The rate of rotation of the rotor is controlled for promoting decarboxylation of the cannabinoid compound solution to form a decarboxylated cannabinoid THC, CBD, CBC or CBG product through interaction with UV light, while minimizing temperature and shear degradation of the molecules of the cannabinoid compound.

In some embodiments, cavitation of the cannabinoid compound solution will be controlled so as to induce nucleation of the compound to form seed crystals, and for distributing the seed crystals substantially uniformly throughout the cannabinoid compound solution. In other embodiments, depending upon the cannabinoid being subjected to treatment, formation seed crystals may not be necessary.

The rotor-stator design of the hydrodynamic cavitation apparatus allows for high flow rates of the feed stock that can be opaque, that contain solids, or that have high viscosity. Further, the hydrodynamic cavitation apparatus can operate substantially continuously, making the hydrodynamic cavitation apparatus and method of this present disclosure suitable for decarboxylation of cannabinoid compounds within a feed stock solution at commercially desirable flow rates. Finally, the process can be tuned to provide highly reliable results and high yield. The process is aided by the low temperature, low pressure and low shear environment of the cavitation zone so as to not damage other compounds of interest.

The hydrodynamic cavitation apparatus technology disclosed herein and as disclosed in U.S. Pat. No. 10,011,804 and United States Patent Publication Nos. YW6454344=4568E5$erh$2019/0169479A1, the disclosures of which is incorporated by reference as if set forth fully herein, coupled with a clear glass housing and UV light can use its tremendous mixing ability to provide "surface refresh" constantly bringing fresh oil to the light/glass interface. This means samples even opaque samples, with no ability for light to penetrate, can be thoroughly treated. Work done in University studies with opaque liquids using the hydrodynamic cavitation apparatus technology has shown the ability to obtain essentially 100% UV treatment. The cavitation generated within the cannabinoid compound solution is controlled by varying the RPM of the rotor between about 0 RPM and about 3600 RPM to optimize UV reaction while minimizing temperature and shear degradation.

The application of cavitation events into the cannabinoid compound solution and exposure to and interaction with UV light as the cannabinoid compound solution is passed through the cavitation apparatus could potentially provide an opportunity to decarboxylate cannabis and hemp with enhanced productivity as the decarboxylation process could be accomplished in seconds versus hours, and further can be accomplished at temperatures low enough to minimize the loss of the temperature sensitive compounds, such as terpenes.

In addition to decarboxylation of common cannabinoids like CBDA or THCA, it should be possible to convert common cannabinoids into some rarer cannabinoids through similar treatment. For example, in hemp, CBGA is the base cannabinoid from which the other cannabinoids are derived through enzymatic, oxidative, photo-oxidative, heat or photochemical processes. For example, CBDA can be converted to CBEA through phot-oxidation. This new species could then also be decarboxylated.

The hydrodynamic cavitation apparatus technology disclosed herein and as disclosed in U.S. Pat. No. 10,011,804 and United States Patent Publication No. 2019/0169479A1, the disclosures of which is incorporated by reference as if set forth fully herein, has been shown highly effective at enhancing UV energy exposure, especially in bacteria. By way of example, as shown in the table below, in work conducted at the University of Georgia, where no UV is indicated, that equals basically no reduction in bacteria. It also appears that no cavitation equals basically no reduction. But together, the cavitation and UV application provide a 3 log reduction in bacteria (which is equal to 99.9% effectiveness of the treatment).

TABLE 3

Inactivation of *E. coli* ATCC 25922 in Skim Milk (pH = 6.0) Processed in an Ultraviolet-Shockwave Power Reactor at an Initial Temperature of 15 ± 1° C. with Varying Rotational Speeds (n = 4; Mean Values).[a]

| | | Treatment (rpm) | | | | | |
|---|---|---|---|---|---|---|---|
| Treatment (rpm) | UV (253.7 nm) | $T_{in}$ = (° C.) | $T_{out}$ = (° C.) | Floor rate (L/min) | $N_o$ ($Log_{10}$) | N ($Log_{10}$) | Log reduction ($Log_{10}$) |
| 0 - Control | No | 15.8 | 15.8 | 1.5 | 7.11 | 7.11 | 0' |
| 0 - Control | Yes | 15.8 | 15.8 | 1.5 | 7.11 | 7.03 | 0.08° |
| 600 | Yes | 15.8 | 15.8 | 1.5 | 7.11 | 6.79 | 0.33° |
| 1200 | Yes | 15.8 | 16.4 | 1.5 | 7.11 | 6.57 | 0.54° |
| 1800 | Yes | 15.8 | 18.6 | 1.5 | 7.11 | 5.78 | 1.33° |
| 2400 | Yes | 15.8 | 23.1 | 1.5 | 7.11 | 3.86 | 3.25° |
| 3000 | Yes | 15.8 | 29.7 | 1.5 | 7.11 | 3.84 | 3.24° |
| 3600 | Yes | 15.8 | 40.8 | 1.5 | 7.11 | 3.88 | 3.24° |
| 3800 | No | 15.8 | 44.4 | 1.5 | 7.11 | 6.97 | 0.15° |

[a]n = 4; Means Followed by Same Letter in Column do not Differ Significantly ($\alpha$ = 0.05) According to ANOVA and SNK Analyses (Detection >10 CFU/mL).
M412 Journal of Food Sciences-Vol. 72, Nr. 9, 2007

The combination of UV light and cavitation as provided by the apparatus and method of the present disclosure is designed and configured to provide an enhanced decarboxylation reaction in cannabis to enable reductions in concentration losses during decarboxylation. All CBD produced that will not be smoked or baked (the vast majority) should be expected to be decarboxylated. Below is a chart showing typical losses in decarboxylation. Although CBD prices have been falling rapidly with increased production, we are still talking about a product that sells for thousands of dollars per kg. Therefore, taking significantly less losses and/or making higher yields of the active decarboxylated form is of extreme value to the market.

The Relative Loss for the Total Molar Concentration
(Sum of Acidic Reactants and Neutral Products)
Upon Completion of Decarboxylation

| Decarboxylation reaction | Form | Temperature (° C.) | Relative loss in total molar concentration (%) |
|---|---|---|---|
| THCA-A→THC | Extracts | 110 | 7.94 |
| CBDA→CBD | Extracts | 110 | 18.05 |
| CBDA→CBD | Extracts | 130 | 25.2 |
| CBGA→CBG | Extracts | 110 | 52.67 |
| CBDA→CBD | Pure Standard | 110 | 13.75 |

CBD, cannabidiol; CBDA, cannabidiolic acid; CBG, cannabigerol; CBGA, cannabigerolic acid; THC, tetrahydrocannabinol; THCA-A, tetrahydrocannabinolic acid-A.

Figure 3:
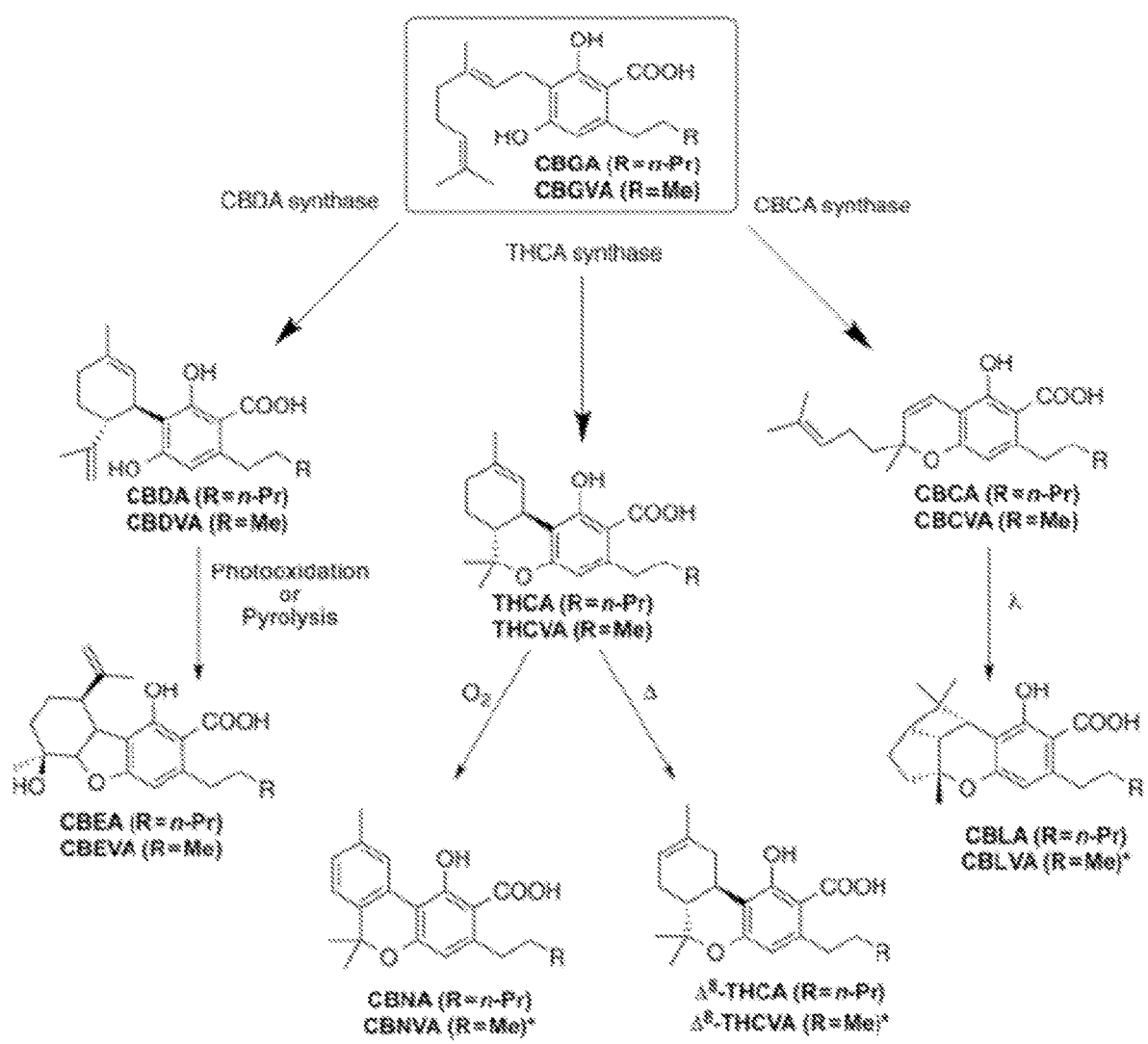
FIG. 3 illustrates a series of reactions showing embodiments of the interconversion of CBDA, THCA and CBCA cannabinoids according to principles of the present disclosure.

FIG. 3 shows a series of reactions that illustrate the interconversion of CBDA, THCA and CBCA cannabinoids under processes of photo-oxidation or pyrolysis and/or decarboxylation carried out according to the methods of the present disclosure. Typical thermal decarboxylation (simple heating of the product for extended time) can lead to degradation of the reactants and/or resultant desired product. Higher temperatures can result in faster decarboxylation, as would be expected, however this also leads to greater product loss. Cannabinoids such as CBG are also more sensitive to thermal degradation as compared to THC or CBD.

The controlled cavitation apparatus/technology disclosed herein, coupled with a clear glass housing and UV light can use the tremendous mixing ability of the cavitation device to provide a substantially continuing "surface refresh" whereby fresh oil is brought to the light/glass interface at a substantially consistent and relatively constant rate. This means samples even opaque samples with generally no ability for light to penetrate therethrough, can be thoroughly treated. The application of UV light can also react to produce oxidative species such as ozone, peroxide or radicals. In a similar fashion the controlled cavitation apparatus/technology can be coupled with electrodes and use its tremendous mixing ability to provide "surface refresh" to allow electrochemical reactions to occur in a similar fashion. Finally, the controlled cavitation apparatus/technology can provide excellent mixing of added oxidative species such as ozone, oxygen or peroxide or those created in situ.

In addition to providing surface refreshment for more thorough UV light exposure/contact of opaque liquids without immersion, the use of the hydrodynamic cavitation apparatus, such as a ShockWave Power Reactor™ and as disclosed in U.S. Pat. No. 10,011,804 and United States Patent Publication No. 2019/0169479A1, is provides higher efficiencies in mass transfer for mixing of dissimilar fluids. This includes gas-liquid mixing for purposes of oxidation. Using a similar setup and conditions found for UV decarboxylation photo-oxidation (the coupling of UV treatment with simultaneous oxidation) could allow for the conversion of one cannabinoid species into another. This could allow for the synthesis of more valuable or rare cannabinoids from ones more commonly found in hemp. Depending upon the starting cannabinoid this would be accomplished by interaction with either UV light or oxidizing agents alone or in combination.

The application of these results potentially provides an opportunity to easily create higher value, rarer cannabinoids. The advantages to this would be productivity as it could potentially be accomplished in seconds versus hours, as part of a substantially continuously operable process, and at temperatures low enough to minimize the loss of other desirable temperature sensitive compounds, such as terpenes, which are often degraded or volatized at standard decarboxylation temperatures. For example, the decarboxylation or photo-oxidation of the cannabinoid compounds can be conducted at lower temperatures that can range from approximately 100° Celsius to approximately 140°, or in some embodiments, less than approximately 100°-110° Celsius. The pressures at which cavitation can be induced in the cannabinoid compound solution further can be maintained at lowered pressures—for example, between approximately 1 psi to approximately 50 psi, although other, greater or lower pressures also can be used. The lower pressure and temperature allows for less expensive capital equipment to be utilized and for reactions to occur under safer and essentially ambient conditions.

The present disclosure has been described above in terms and within the context of preferred embodiments and methodologies considered by the inventor to represent the best modes of carrying out the present disclosure. It will be understood, however, that the present disclosure certainly is not limited to the illustrated embodiments and methodologies. A wide range of additions, deletions, and modifications, both subtle and gross, might well be made to the illustrated embodiments by the skilled artisan without departing from the spirit of scope of the present disclosure, which is delineated only by the claims. For example, while it is preferred to dry the cannabis plant and to chop the dried plant into small pieces, this is not necessarily a limitation of the present disclosure. It is possible to carry out the methodology of the present disclosure with undried cannabis plant material that is either chopped into pieces or left as a whole plant.

Still further, various advantages and aspects of the embodiments of the disclosure will become apparent and more readily appreciated from the following detailed description of the embodiments and the claims, taken in conjunction with the accompanying drawings. Moreover, it is to be understood that both the foregoing disclosure is exemplary and intended to provide further explanation without limiting the scope of the disclosure as claimed.

What is claimed:

1. A method of converting a cannabinoid compound solution using controlled hydrodynamic cavitation, the method comprising:
 a. feeding a stream of the cannabinoid compound solution into a cavitation apparatus having an inlet, an outlet, a rotor having a series of cavitation inducing features therealong, and a cavitation cavity or stator with one or more transparent outer walls and within which a cavitation zone is defined;
 b. directing the cannabinoid compound solution to flow through the cavitation zone of the cavitation apparatus;
 c. generating cavitation within the cannabinoid compound solution in the cavitation zone;
 d. during cavitation, subjecting the cannabinoid compound solution to UV light transmitted through the one or more transparent outer walls;
 e. controlling cavitation generated within the cannabinoid compound solution to optimize UV reaction with the cannabinoid compound solution while minimizing temperature and shear degradation; and
 f. promoting conversion of the cannabinoid compound solution to form a synthesized cannabinoid THC, CBD, CBC, CBG, CBNA, CBEA, CBLA product, or combinations thereof through interaction with UV light, with oxygen, with reagents, or combinations thereof.

2. The method of claim 1, wherein generating cavitation within the cannabinoid compound solution is conducted at a temperature of approximately 100° to approximately 140° Celsius.

3. The method of claim 1, wherein generating cavitation within the cannabinoid compound solution is conducted at a pressure of approximately 1 psi to approximately 50 psi.

4. The method of claim 1, wherein controlling cavitation generated within the cannabinoid compound solution comprises varying the RPM of the rotor between about 0 RPM and about 3600 RPM.

5. The method of claim 1, wherein directing the cannabinoid compound solution to flow through the cavitation apparatus comprises feeding the cannabinoid compound solution in a substantially continuous fluid stream of the cannabinoid compound solution through the inlet and into the cavitation cavity or stator where the cannabinoid compound solution passes between the rotor and the cavitation cavity or stator.

6. The method of claim 1, wherein the cannabinoid compound solution comprises an "crude" cannabinoid solution containing multiple cannabinoids, terpenes and other chemical compounds extracted from cannabis.

7. The method of claim 1, wherein the stream of the cannabinoid compound solution comprises a viscous stream.

8. The method of claim 1, wherein the stream of the cannabinoid compound solution comprises solid materials.

9. The method of claim 1, wherein the cannabinoid compound solution comprises a solution that is opaque.

10. The method of claim 1, wherein the cannabinoid compound solution comprises a solution of THCA, CBDA, or CBCA biosynthesized from CBGA.

11. The method of claim 1, wherein promoting conversion of the cannabinoid compound solution comprises decarboxylating the cannabinoid compound solution to form synthesized cannabinoid THC, CBD, CBC, CBG, or combinations thereof, through interaction of the cannabinoid compound solution with UV light.

12. The method of claim 1, wherein promoting conversion of the cannabinoid compound solution comprises decarboxylating a CBCA compound to CBLA through interaction with UV light.

13. The method of claim 1, wherein promoting conversion of the cannabinoid compound solution comprises promoting oxidation of a THCA compound to CBNA through interaction with oxygen or other oxidative species either added or created in situ.

14. The method of claim 1, wherein promoting conversion of the cannabinoid compound solution comprises promoting oxidation of a CBDA compound to CBEA through interaction with UV light.

15. The method of claim 1, wherein the cavitation apparatus comprises electrodes configured to enable electrochemistry and the production of oxidative species in situ within the cannabinoid compound solution.

16. The method of claim 15, wherein the oxidative species comprise ozone, peroxide, radicals, or combinations thereof.

17. The method of claim 1, wherein feeding the stream of the cannabinoid compound solution comprises feeding a substantially consistent flow of the cannabinoid compound solution through the cavitation zone.

18. The method of claim 1 wherein promoting conversion of the cannabinoid compound solution comprises exposing the cannabinoid compound solution to UV light and to ozone or other reactant to promote pasteurization of the cannabinoid compound solution.

19. The method of claim 1, wherein generating cavitation within the cannabinoid compound solution in the cavitation zone further comprises inducing nucleation of the cannabinoid compound solution to form seed crystals therein; and wherein controlling cavitation generated within the cannabinoid compound solution further comprises distributing the seed crystals substantially uniformly throughout the cannabinoid compound solution.

20. A method of converting a cannabinoid compound solution using controlled hydrodynamic cavitation, the method comprising:
 a. feeding a stream of the cannabinoid compound solution into a cavitation apparatus having an inlet, an outlet, a rotor having a series of cavitation inducing features therealong, and a cavitation cavity or stator with one or more and within which a cavitation zone is defined;
 b. directing the cannabinoid compound solution to flow through the cavitation zone of the cavitation apparatus;
 c. generating cavitation within the cannabinoid compound solution in the cavitation zone, wherein the cavitation is conducted at a temperature of approximately 100° to approximately 140° Celsius;
 d. controlling cavitation generated within the cannabinoid compound solution to optimize UV reaction with the cannabinoid compound solution while minimizing temperature and shear degradation; and e. promoting conversion of the cannabinoid compound solution to form a synthesized cannabinoid THC, CBD, CBC, CBG, CBNA, CBEA, CBLA product, or combinations thereof through heating with oxygen, with reagents, or combinations thereof.

21. The method of claim 20, further comprising subjecting the cannabinoid compound solution to UV light transmitted through one or more transparent outer walls of the cavitation apparatus during cavitation of the cannabinoid compound solution.

22. The method of claim 20, wherein promoting conversion of the cannabinoid compound solution comprises decarboxylating the cannabinoid compound solution to form synthesized cannabinoid THC, CBD, CBC, CBG, or combinations thereof, through interaction of the cannabinoid compound solution with UV light.

23. The method of claim 20, wherein the cavitation generated within the cannabinoid compound solution is conducted at a pressure of approximately 1 psi to approximately 150 psi.

24. The method of claim 20, wherein controlling cavitation generated within the cannabinoid compound solution comprises heating the cannabinoid compound solution without a heat transfer surface or substantial temperature gradient for reduced thermal degradation of cannabinoids.

25. The method of claim 20, wherein promoting conversion of the cannabinoid compound solution comprises promoting oxidation of a THCA compound to CBNA through interaction with oxygen or other oxidative species either added or created in situ.

26. A method of converting a cannabinoid compound solution using controlled hydrodynamic cavitation, the method comprising:
a. feeding a stream of the cannabinoid compound solution into a cavitation apparatus having an inlet, an outlet, a rotor having a series of cavitation inducing features therealong, and a cavitation cavity or stator with one or more and within which a cavitation zone is defined;
b. directing the cannabinoid compound solution to flow through the cavitation zone of the cavitation apparatus;
c. generating cavitation within the cannabinoid compound solution in the cavitation zone;
d. during cavitation, subjecting the cannabinoid compound solution in the cavitation zone to interaction with at least one of UV light transmitted through one or more transparent outer walls of the cavitation apparatus, heating with oxidative species, heating with reagents, or combinations thereof;
c. controlling cavitation generated within the cannabinoid compound solution to optimize UV reaction with the cannabinoid compound solution while minimizing temperature and shear degradation; and
d. promoting conversion of the cannabinoid compound solution to form a synthesized cannabinoid THC, CBD, CBC, CBG, CBNA, CBEA, CBLA product, or combinations thereof through interaction with UV light, with oxygen, with reagents, or combinations thereof.

27. The method of claim 26, wherein controlling cavitation generated within the cannabinoid compound solution causes heating of the cannabinoid compound solution without a heat transfer surface or temperature gradient for reduced thermal degradation of cannabinoids.

28. The method of claim 26, wherein generating cavitation within the cannabinoid compound solution is conducted at a temperature of approximately 100° to approximately 140° Celsius.

29. The method of claim 26, wherein controlling cavitation generated within the cannabinoid compound solution comprises varying the RPM of the rotor between about 0 RPM and about 3600 RPM.

* * * * *